United States Patent [19]

Binder et al.

[11] 4,036,724

[45] July 19, 1977

[54] DEVICE FOR THE CONTINUOUS DETERMINATION OF CARBON MONOXIDE CONTENT OF AIR

[75] Inventors: Horst Binder, Petterweil; Reinhard Knodler, Diedenbergen; Alfons Kohling, Eschborn; Gerd Sandstede, Frankfurt am Main, all of Germany

[73] Assignee: Dragerwerk Aktiengesellschaft, Germany

[21] Appl. No.: 580,532

[22] Filed: May 23, 1975

Related U.S. Application Data

[63] Continuation-in-part of Ser. No. 455,505, March 27, 1974, abandoned.

[30] Foreign Application Priority Data

Apr. 2, 1973 Germany ............................. 2316365

[51] Int. Cl.² ............................................. G01N 27/46
[52] U.S. Cl. ............................ 204/195 R; 204/195 P; 204/1 T
[58] Field of Search ............ 136/86 R, 86 D, 120 FC; 204/1 T, 1 N, 1 F, 1 K, 195 R, 195 P

[56] References Cited

U.S. PATENT DOCUMENTS

| 3,287,169 | 11/1966 | Rogers | 136/86 D |
| 3,432,355 | 3/1969 | Niedrach et al. | 136/86 D |
| 3,622,487 | 11/1971 | Chand | 204/1 N |
| 3,649,361 | 3/1972 | Paynter et al. | 136/86 D |
| 3,852,169 | 12/1974 | Kring et al. | 204/195 R |

OTHER PUBLICATIONS

Jasimshi, "High-Energy Batteries", 1967, pp. 79-81.
Hamill et al., "Principles of Physical Chemistry", 1959, p. 425.

*Primary Examiner*—T. Tung
*Attorney, Agent, or Firm*—McGlew and Tuttle

[57] ABSTRACT

The device continuously determines the carbon monoxide content of air in the emission and immision range, and comprises an electrochemical cell including an acid electrolyte with a cathode and a diffusion anode in the electrolyte, the anode being depolarizable by carbon monoxide in the acid electrolyte. A current measuring device measures the current between the anode and the cathode responsive to detection of a gas containing carbon monoxide effective on the diffusion anode. The cathode is made of an unpolarizable material whose oxidation potential is so high that no oxygen reduction takes place at the anode. The cell functions without an external current source, and the current measuring device is connected to directly across the anode and the cathode. The cathode contains substances with an oxidation potential of from 1000 to 1300 millivolts relative to a hydrogen electrode in the same electrolyte. The cathode advantageously contains oxides or mixed oxides of transition metals, or manganates, or cobaltates, a preferred material for the cathode being manganese dioxide ($MnO_2$).

6 Claims, 3 Drawing Figures

DEVICE FOR THE CONTINUOUS DETERMINATION OF CARBON MONOXIDE CONTENT OF AIR

CROSS REFERENCE TO RELATED APPLICATION

This application is a continuation-in-part of application Ser. No. 455,505, filed Mar. 27, 1974, now abandoned

FIELD AND BACKGROUND OF THE INVENTION

This invention relates to devices for determining contaminants in gases and, more particularly, to a new and useful electrochemical cell for determining the amount of carbon monoxide present in a gas.

Carbon monoxide is a noxious substance which is produced in every combustion of fuels containing carbon, be it in open flame (domestic fuel) or in the cylinder of an internal combustion engine. In addition, emission sources include production processes in commercial plants, such as, for example, blast and cupola furnaces in the steel making industry. Carbon monoxide thus appears in the air of cities and at work places in concentrations having great fluctuations.

There are numerous reports on the noxious effect of carbon monoxide on the human organism; see, for example, G. Malorny in "Staub-Reinhaltung der Luft", Vol. 32, pages 132-142 (1972). In this paper are indicated maximum immission concentration for carbon monoxide: 8 ppm for 24 h; 16 ppm for 8 h and 80 ppm for h.

The toxicity of carbon monoxide makes it necessary to detect both its emission and its distribution in the environment, and to measure its concentration at points at which persons are endangered, such as, for example, in large cities at heavily congested traffic intersections, in tunnels and in parking spaces, and also a work places in factories, mines, etc.

For the quantitative determination of carbon monoxide, there is a great number of methods, see for example THOENES in "Staub-Reinhalting der Luft", Vol. 32, pages 46 –49 (1972 ). Beside methods using direct chemical reaction (ORSAT principle), the determination by means of gas chromatography and infrared absorption has been very much developed and many firms offer sophisticated apparatus for the continuous determination of the carbon monoxide content. These known devices are, however, utilizable only in stationary locations, because of the size and the weight of the instruments and the dependence on an electric supply line. In this sense, also the special determination installations mounted on vehicles are considered as stationary. Single measurements can also be conducted by means of known carbon monoxide visual detection tubes (K. Grosskopf, "Angew. Chemie", Vol. 63, pages 306 –308, 1962) in the emission and also in the immission range. The necessary time is small and less than 1 minute is necessary for a determination. The disadvantage, however, is the discontinuity of operation.

There is a known electrochemical apparatus for determination of carbon monoxide concentration (H. W. Bay et al, "International Laboratory", September, October 1972, pages 37–41). The cell of this apparatus, which is an electrochemical half-cell, consists of a measuring electrode, a reference electrode and a counterelectrode. The potential of the measuring electrode is measured in respect to the reference electrode and it is regulated to an adjustable value by means of an electronic potentiostat (instrument for maintaining constant a predetermined electrode potential). At this potential, the carbon monoxide is oxidized electrochemically at the measuring electrode, with release of electrons, and the strength of the current is a measure for the carbon monoxide content of the gas being analyzed. The necessary current supply for the potentiostat and for a gas pump is derived from an electronic potentiostat with the respective current supply renders the apparatus expensive and susceptible to troubles. Besides, the accuracy and the reproducibility of the results of determinations are impaired by the continuous water vapor exchange between the electrolyte and the air flowing past.

SUMMARY OF THE INVENTION

The invention provides a handy and easy to use device for the continuous determination of carbon monoxide content in air. This problem is solved by means of an electrochemical cell means and without supplying a current to the cell and at any time and at any place, to make determinations very easily. Consequently this cell is suitable as a warning device for work places endangered by carbon monoxide. An important advantage is that the inventive apparatus is ready for operation without time for preparation and can be handled by unskilled operators.

The acid electrolyte is immobilized in a known manner. A sensitive microammeter is suitable for measuring the short circuit current between the two electrodes. As long as the air does not contain any carbon monoxide, the diffusion anode of the cell is fully polarized, i.e. it has the same potential as the unpolarized cathode, so that no current flows. If carbon monoxide is present at the diffusion anode, it is depolarized and a current flows which is proportional to the carbon monoxide concentration according to FICK's diffusion law.

The cell of the invention is so constructed that it responds also to carbon monoxide concentrations within the immission range. It can, however, also be utilized in the emission range by adapting the microammeter or the instrument for measuring the electrode short circuit current, or by adapting the external energy source connected to its electrodes and the voltages which appear amount to only a few mV, it is absolutely intrinsically safe, so that determinations can be carried out also in spaces where there is an explosion hazard. The cell is always ready for operation and can be operated continuously. In the most simple embodiment, by the convection which is usually always present, as through a loosely fitting ring in front of the anode, fresh air is regularly conducted to the cell. The time of response is small, and the current changes in the few seconds after a change of concentration. The new value of the determination is displayed in less than one minute. The function of the cell is independent of its position and is insensible with respect to movement and concussions.

The polarizable diffusion anode of the inventive cell consists in general of two layers, namely a hydrophobe diffusion layer of polytetrafluoroethylene (PTFE), and a porous hydrophile active layer. This active layer is composed of the catalyst, a conductibility additive, preferably graphitized coal or tungsten bronze, and a thermoplast, such as polyethylene or PTFE, as a binder. For this anode, the catalysist to be considered are first of all platinum or platinum-metal alloys particularly in the form of Raney-metal or Raney-alloy.

The carbon monoxide is oxidized to $CO_2$ with release of electrons on the catalyst of the anode following the equation $CO + H_2O \rightarrow CO_2 + 2H^+ + 2e^-$. The advantage of the use of Raney catalyst over other conventional commercial (platinum) catalysts is that, after a short aging phase, they exhibit a relatively constant surface and herewith a constant electrochemical activity. Consequently recalibrations are necessary only at long intervals. It is, however, known that the oxidation of carbon monoxide is nearly completely inhibited on platinum catalysts by absorption of carbon monoxide molecules (H. BINDER et al., but this happens only at potentials below 700 mV relative to a hydrogen electrode in the same electrolyte. Further, on a platinum electrode in acid electrolyte, oxygen undergoes a cathodic reduction in the range below 1000 mV, which means that a current flows which is opposed to the carbon monoxide oxidation. Since the oxygen content of the gas to be analyzed is always higher than the carbon monoxide content, this current would completely mask the effect of the determination. However, in accordance with the invention, these effects of inhibiting the carbon monoxacle oxidation and reduction of the oxygen are precluded by selecting a cathode material with a sufficiently high oxidation potential, generally over 1000 mV.

According to a preferred embodiment of the invention, oxides or mixed oxides of the transition metals are employed as cathode materials. Particularly suitable are maganese oxides and cobalt spinels which contain nickel, copper, or silver as cations. These substances have a high hydrogen electrode in the same electrolyte. They are all electrochemically reducible at a high current density without disturbing potential losses. They absorb the electrons released in the oxidation of the carbon monoxide. In this case of $MnO_2$, this is reduced to bivalent mangenese ion according to the equation:

$$MnO_2 + 4H^+ + 2e^- \rightarrow Mn^{2+} + 2H_2O$$

Due to the small currents which flow in the cell of the invention, the oxides necessary for long operation periods can be deposited in sufficient amounts in the cell.

Since these oxides have, in general, a poor conductivity conductive substances are also included (alike the diffusion electrode), which have stabiltiy in the acid electrolyte. The conductive substances in the diffusion electrode must have a small surface and few pores, so that the gas exchange may occur rapidly and the sttting time of the carbon monoxide indication not be delayed by the conveying of the carbon monoxide in the pores.

All strong acids, such as perchloric acid, sulfuric acid, or phosphoric acid, can be utilized as electrolyte. A moderately concentrated phosphoric acid has proven very suitable, since herewith the water absorption and release through the diffusion layer remain the smallest. It is advantageous whe the acid is immobilized, for example by absorption in asbestos felt or in aluminum oxide powder. By this means the cell can be operated in any position, by contrast to a cell with free electrolyte.

An object of the invention is to provide an improved carbon monoxide detection device in the form of an electrochemical cell, and which makes it possible to provide a continuous determination of the carbon monoxide content of a gas while operating without any separate current source connected to its electrodes.

Another object of the invention is to provide such an electrochemical cell including a cathode and a diffusion anode arranged in an acid electrode, and in which the anode is depolarizable by carbon monoxide in the electrolyte, and which also includes current measuring means connected between the anode and the cathode and indicating the current generated by the cell when a gas containing carbon monoxide is directed into the vicinity of the anode.

A further object of the invention is to provide a device for the continuous determination of carbon monoxide in a gas which is simple in design, rugged in construction and economical to manufacture.

For an understanding of the principles of the invention, reference is made to the following description of typical embodiments thereof as illustrated in the accompanying drawing.

GENERAL DESCRIPTION OF THE PREFERRED EMBODIMENTS

Figure 1:
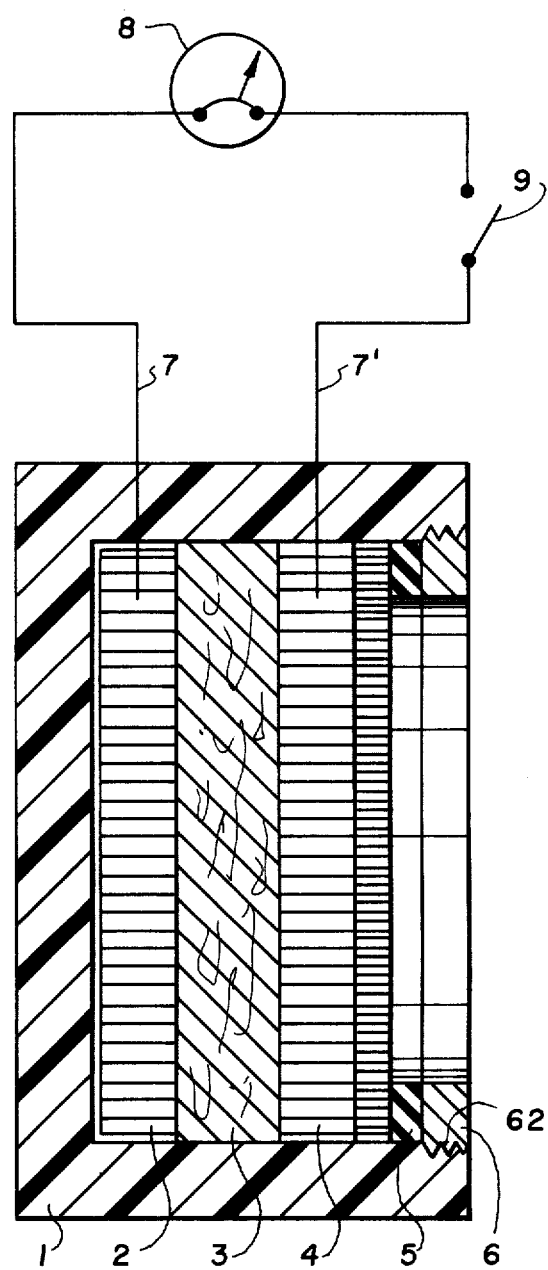
FIG. 1 is a somewhat schematic sectional view of a device embodying the invention for determining carbon monoxide content of the gas.

The present invention provides a device for determining the carbon monoxide content in a gas such as air, and which is capable of continuous operation and without a separate source of power connected to its electrode.

The preparation of the electrodes according to a method that was tested and proved successful in which the diffusion layer and the active layer are made in one work step, and the construction of the cell of the invention, are described in the following example.

EXAMPLE 400 mg PTFE powder of grain size of 30 um are suspended in about 10 ml propanol and filtered on a suction filter with an diameter of 48 mm. This layer becomes the diffusion layer of the electrode. For the active layer, a second suspension is prepared of 400 mg PTFE powder, 400 mg graphitized coal (below 32 um), 100 mg graphite felt ground with mortar and pestle, and 130 mg platinum-aluminum alloy of the composition $PtAL_3$ (below 32 um) in 15 ml propanol and poured onto the still moist PTFE layer. Then, a gold or tantalum gauze with a welded contact wire is introduced into the suspension and thereafter also filtered. A manageable electrode is obtained, which at first is dried at 100° C and subsequently sintered under a moderate load of 10 to 15 p/cm² during 2 hours at 370° C. Finally the aluminum of the $PtAL_3$ is removed by dissolving it in a moderately concentrated potassium hydroxide solution. Thus, a stable electrode of 48 mm diameter is obtained with a porosity of about 50 vol. %. In the active layer, there are about 5 mg platinum per cm². This amount is sufficient to impart to the electrode such a high activity that it functions always in the diffusion limiting current range. It is only as long as this condition is met that there results a linear dependence of the current on the carbon monoxide concentration.

The cathode can be made according to the same method. For example, a suspension is prepared of 600 mg PTFE, 400 mg $Na_{0.25}WO_3$ as a conductivity additive and 1000 mg $MnO_2$, and processed further as described above. It is here advantageous previously to mix the $MnO_2$ intimately with the sodium tungsten bronze.

For preparing the immobilized electrolyte, asbestos fibers are introduced into a 15 N phosphoric acid until a brushable paste is obtained.

The assembling into a cell ready to operate, as shown in the drawing of an embodiment of the invention, is relatively simple:

Into a receptacle 1 made of electrically non-conductive plastic material, for example of plexiglass, are introduced in succession a cathode 2, an electrolyte 3, immobilized with asbestos fibers, and a diffusion electrode or anode 4 with the active layer oriented towards the electrolyte 3. These parts are secured by a threaded ring 6 threaded on internal threads 62 over a gasket 5. The ring 6 is made of acid-resistant steel. The contact wires 7, 7' of electrodes 2, 4, are introduced through previously prepared holes and sealed in with an acid-resistant cement. Cathode 2 and anode 4 are directly interconnected through current measuring means in the form of a microammeter 8 and short circuited thereby.

In order to put the cell into operation, all that is necessary is to close switch 9. For a short period after closure of switch 9, a high intensity current flows, which polarizes the anode 4 completely. The cell is then ready for determinations and, after calibration with a test gas of known carbon monoxide content, indicates, at microammeter 8, the carbon monoxide concentration in the environment. Due to the existing convection through the open loosely fitting ring 6 in receptacle 1, fresh air is delivered continuously to diffusion anode 4. This simplest construction of the cell, as shown in FIG. 1, is primarily designed for determinations of carbon monoxide contents at carbon monoxide endangered work places.

Figure 2:
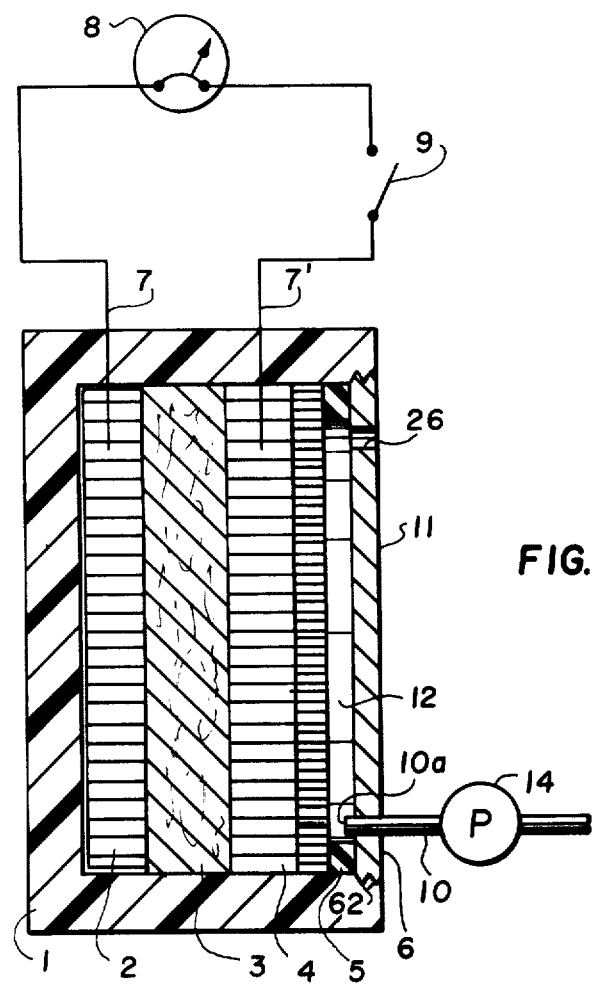
FIG. 2 is a view, similar to FIG. 1, of another embodiment of the invention.
Figure 3:
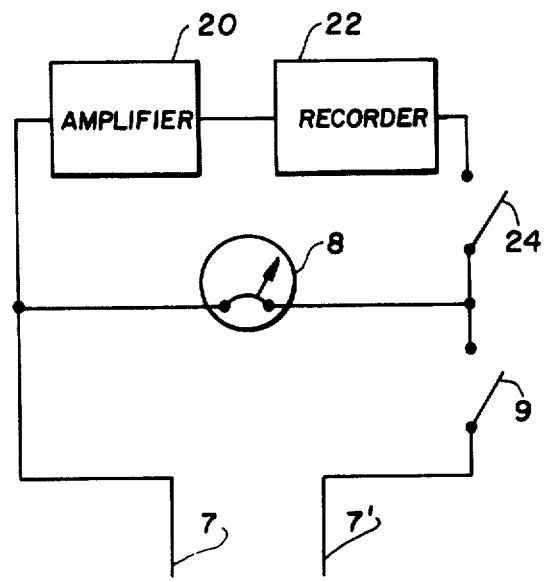
FIG. 3 is a schematic wiring diagram illustrating how an amplifier and a recorder can be connected to the cell of the invention.

The simple cell shown in FIG. 1 may be enlarged on the gas side, as shown in FIG. 2, as well as on the display side, as schematically illustrated in FIG. 3. Referring to FIG. 2, the open steel ring 6 is closed by a metal plate 11 secured therein in substantially sealed relation. This closing plate 11 has a gas inlet pipe 10 extending therethrough and having a discharge opening 10a in a chamber 12 defined between closing plate 11 and diffusion anode 4. The gas to be analyzed can be supplied through pipe 10 by means of a manual or an electric pump 14, and flows out through an outlet opening 26 in closing plate 11. With the arrangement of FIG. 2, it is possible, for example, to scan, with a probe, suspect emission sources, such as flange connections, valves, etc.

As schematically indicated in FIG. 3, an amplifier 20 and a conventional recorder, printer and warning device 22 may be connected in parallel with microammeter 8 through the medium of a switch 24. In FIG. 3, the cell itself has been omitted, but it will be understood the connections or leads 7 and 7' are secured directly to the cathode 2 and the diffusion anode 4. With the arrangement of FIG. 3, the manageability and the independence from supply systems, such as a battery or a power line, is affected to some extent, but this can be tolerated in many cases of application.

While specific embodiments of the invention have been shown and described in detail to illustrate the application of the principles of the invention, it will be understood that the invention may be embodied otherwise without departing from such principles.

What is claimed is:

1. An electrochemical cell, for the continuous determination of the carbon monoxide content of a gas, such as air, in the emission and immission ranges, comprising, in combination, a receptacle containing an acid electrolyte; a cathode having a surface in contact with the electrolyte; a diffusion anode, depolarizable by carbon monoxide, having an inner active layer in contact with the electrolyte and a superposed outer hydrophobe gas diffusion layer out of contact with the electrolyte; means subjecting the anode to the carbon monoxide-containing gas by flow of the gas through said diffusion layer; said anode, at a potential of less than 1000 mV relative to a hydrogen electrode in the same electrolyte, being subject to oxygen-reduction; said cathode being constituted by an unpolarizable material, selected from the group consisting of oxides and mixed oxides of the transition metals, having an oxidation potential of over 1000 mV relative to a hydrogen electrode in the same electrolyte; and current measuring means connected, in short circuiting relation, between said cathode and said anode to polarize said anode to the potential of said cathode so that, in the absence of carbon monoxide, no current flows between said cathode and said anode and so that no oxygen-reduction takes place at said anode; whereby said anode, when subjected to a gas containing both oxygen and carbon monoxide, functions only as an anode for the oxidation of the carbon monoxide and is depolarized relative to said cathode to provide a corresponding current flow through said current measuring means; said cell functioning without any external current source.

2. Electrochemical cell according to claim 1, wherein said cell functions without any external current wherein; said current measuring means consisting of a microammeter connected directly between said anode and cathode and constituting a direct short circuit connection therebetween.

3. Electrochemical cell according to claim 1, wherein said cathode contains substances with an oxidation potential of +1000 to +1200 mV relative to a hydrogen electrode in the same electrolyte.

4. Electrochemical cell according to claim 1, wherein said cathode contains manganates.

5. Electrochemical cell according to claim 1, wherein said cathode contains cobaltates.

6. Electrochemical cell according to claim 1, wherein said cathode contains manganese dioxide.

* * * * *